(12) United States Patent
Eifler (10) Patent No.: US 9,468,781 B2
(45) Date of Patent: Oct. 18, 2016

(54) FASTENING DEVICE FOR STRAPS (75) Inventor: Martin Eifler, Glückstadt (DE)

(73) Assignee: WEINMANN GERATE FUR MEDIZIN GMBH & CO. KG, Hamburg (DE)

( * ) Notice: Subject to any disclaimer, the term of this patent is extended or adjusted under 35 U.S.C. 154(b) by 1140 days.

(21) Appl. No.: 13/399,445

(22) Filed: Feb. 17, 2012

(65) Prior Publication Data
US 2012/0234319 A1 Sep. 20, 2012

(30) Foreign Application Priority Data
Feb. 17, 2011 (DE) .......... 10 2011 011 481

(51) Int. Cl.
*A44B 11/25* (2006.01)
*A62B 18/08* (2006.01)
*A61M 16/06* (2006.01)

(52) U.S. Cl.
CPC .......... *A62B 18/084* (2013.01); *A44B 11/2534* (2013.01); *A61M 16/0683* (2013.01); *Y10T 24/45529* (2015.01)

(58) Field of Classification Search
CPC A62B 18/084; A44B 11/263; A44B 11/266; A44B 11/25; A44B 11/2503; A44B 11/2534; A44B 11/2569; A44B 11/2573; A44B 11/2576; Y10T 24/45581; Y10T 24/45524; Y10T 24/45529; A61M 16/0683
USPC .................. 24/662, 664, 635, 614–616, 625, 24/573.11, 580.1, 607, 619, 627
See application file for complete search history.

(56) References Cited

U.S. PATENT DOCUMENTS

| | | | | |
|---|---|---|---|---|
| 3,407,453 | A * | 10/1968 | Invernizzi ............ | A44C 5/2076 24/594.1 |
| 4,831,694 | A * | 5/1989 | Kong .............................. | 24/625 |
| 5,379,496 | A * | 1/1995 | Krauss ............................ | 24/625 |
| 6,487,761 | B2 * | 12/2002 | Van Tassel ..................... | 24/606 |
| 2005/0199240 | A1 | 9/2005 | Hall | |
| 2005/0223529 | A1 * | 10/2005 | McClelland .................... | 24/130 |

FOREIGN PATENT DOCUMENTS

EP 1360971 B1 8/2008

* cited by examiner

*Primary Examiner* — Abigail Morrell
(74) *Attorney, Agent, or Firm* — Abel Law Group, LLP (57) ABSTRACT

A fastening device for a strap, including a receiving element, a clip with at least one spring element configured for a locking engagement in the receiving element, and a slide moveable relative to the clip so that movement of the slide moves the spring element out of its position of rest for releasing the locking engagement.

20 Claims, 10 Drawing Sheets

FASTENING DEVICE FOR STRAPS

The present application claims priority of DE 10 2011 011 481.5, filed Feb. 17, 2011, the priority of this application is hereby claimed and this application is incorporated herein by reference.

BACKGROUND OF THE INVENTION

The invention relates to a fastening device. The fastening device can be used particularly in the field of medical technology, particularly for a quick release fastening between a head strap or hood and a breathing mask.

Fastening devices for the straps of a breathing mask are already known from the prior art. In particular, fastening means for straps or hoods, which are connected to an eyelet by means of a hook-and-loop fastener and are fastened to the mask body and/or the forehead rest, are widely used. The fastening device of EP1360971B1 includes a clip consisting of lateral spring lugs with operating surfaces and an eyelet to which the straps are fastened. For closing the fastening device by means of the spring lugs, the clip is inserted into a sleeve which has lateral recesses for the operating surfaces of the spring lugs. For releasing the connection, the user must initially press the spring lugs together in order to release the locking engagement and then, while maintaining the pressure on the spring lugs, pull the clip out of the sleeve. The solution known from US2005199240A1 operates according to the same principal. In this case, two separate movements are necessary for releasing the connection between the clip and the sleeve. This is not practical because the fastening device is not within the field of vision of the user and, thus, the user cannot carry out movements required for releasing the device within his/her sight. Other solutions, in which the connection is realized through hooks and eyes, also have the disadvantage described above.

SUMMARY OF THE INVENTION

Therefore, it is the object of the invention to make available a secure fastening device which offers a substantially simpler manipulation for releasing the connection.

In particular, it is an object of the invention to make available a fastening device in which, for releasing the connection, the user only has to apply a force in a defined pulling direction.

In accordance with the invention, the object is met in that the fastening device includes a clip with at least one spring element which is configured for being received for a locking engagement in a receiving means, and in which a slide is moveable relative to the clip, wherein a movement of the slide moves the spring element out of the receiving means for releasing the locking engagement.

The fastening device is composed of at least three parts, namely a clip and a slide, wherein the slide is able to slide relative to the clip, as well as a receiving means.

The strap is fastened to the clip in the area of a strap receiving means. The slide engages around the clip, at least over areas thereof.

The receiving means is preferably connected fixedly or moveably to the mask body or the forehead rest, or is constructed as an integral component of the mask body or the forehead rest.

The slide and/or spring element include at least one inclined surface through which, when the slide is moved relative to the clip, the spring element is deflected from its position of rest.

The slide and/or the clip have at least one guide element along which the relative movement of the slide takes place at least partially.

At least one spring element has at least one locking element which engages at an undercut in the area of the receiving means.

The clip can have two lateral spring elements whose locking elements engage behind an undercut on both sides in the receiving means, and form the locking engagement in this manner.

When inserted into the receiving means, the spring element slides along an inclined insertion surface and is deflected by the wedge and/or lever effect in order to facilitate the complete insertion in this manner.

The clip has a guide web which serves for guiding and centering in the slide, and/or in the receiving pocket.

The clip can be slid into the receiving means with two different orientations because the receiving means is constructed symmetrically and can receive the spring element in both directions.

A rip line at the slide can serve as a quick release system for separating the connection in panic situations.

The spring element has an inclined surface which is acted upon by a surface of the slide when the slide is moved in the direction of the strap eyelet for releasing the connection.

For mounting the slide, the slide is pushed over the clip and, at the same time, the spring element is deflected out of its position of rest by the inclined surface until the slide finds its position behind the stop.

The clip has at one end an eyelet as receiving means for the strap, and in the opposite direction at least one locking element.

Serving for inserting the clip into the receiving pocket are lateral inclined surfaces in the receiving pocket, which act on the inclined surfaces of the spring elements, until the hooks lockingly engage behind the surfaces of the receiving means.

Selected as material of the clip, the slide, and the receiving means, is any suitable, widespread hard synthetic material, such as, for example, POM, PC, or PA, preferably POM.

The slide contains as coating a soft component which completely or partially surrounds the outer surface of the slide, and is connected or glued by the 2K-method to the slide.

After the clip has been deflected from the receiving means, the slide is moved back by the forces resulting from the elastic deformation of the snap-type hook and/or hooks, into its initial position and/or is held at that location.

Subject matter of the invention is also a clip for use in a fastening device according to the invention.

Subject matter of the invention is also a receiving means for use in a fastening device according to the invention.

Subject matter of the invention is also a slide for use in a fastening device according to the invention.

A slight separation of the locking engagement is achieved by pulling the slide for releasing the locking engagement.

A simple separation of the locking engagement can also be achieved by pushing the slide for releasing the locking engagement.

A receiving means for the fastening device in the area of the mask body or the forehead rest is a pocket in which the clip is locked. This receiving means may be connected fixedly or moveably to the mask body or the forehead rest or to a case, or a bag, or a backpack, or may be constructed as an integrated component of the mask body or the forehead rest or case, bag or backpack.

The clip has at one end an eyelet as receiving means for the strap and, in the opposite direction, at least one resilient snap-type hook which can lockingly engage in the receiving pocket in an opening with undercut. A slide serves as an actuating element for releasing the locking engagement of the clip.

BRIEF DESCRIPTION OF THE DRAWING

This is described in the embodiments and illustrated in the figures. In the drawing.

DETAILED DESCRIPTION OF THE INVENTION

Figure 1:
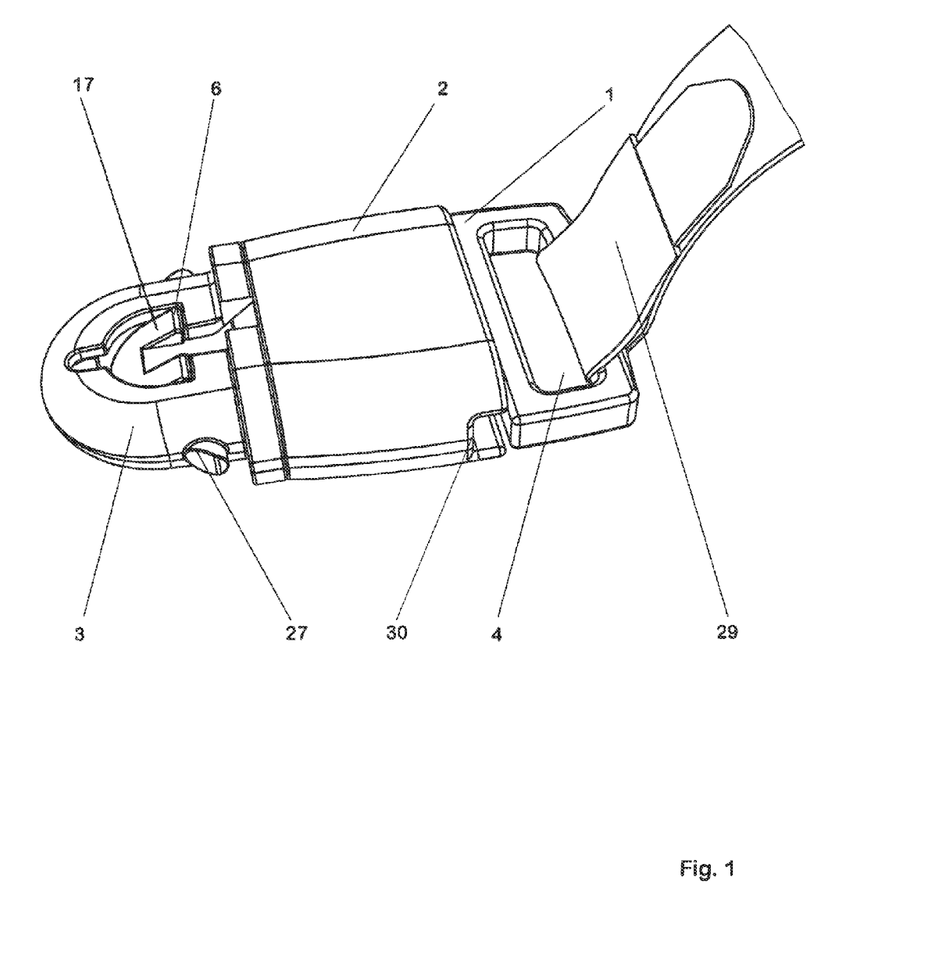
FIG. 1 shows the configuration of a first embodiment of a fastening device.
Figure 2:
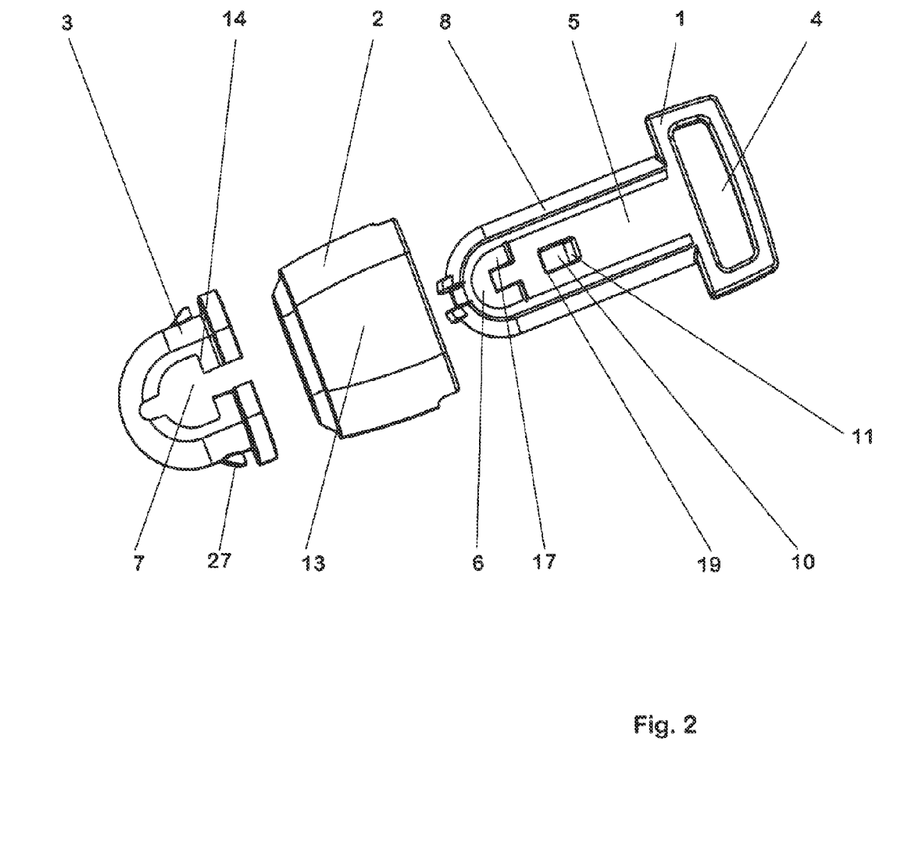
FIG. 2 is an exploded view of the fastening device.
Figure 3:
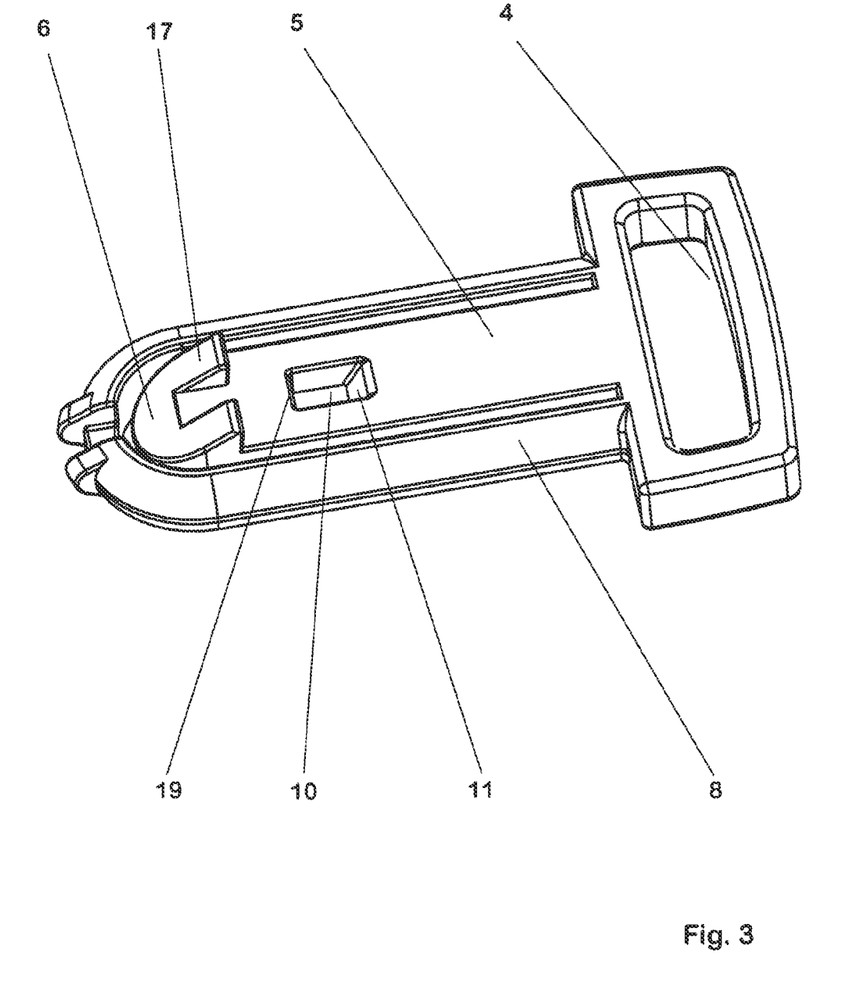
FIG. 3 is a detailed illustration of the clip.
Figure 4:
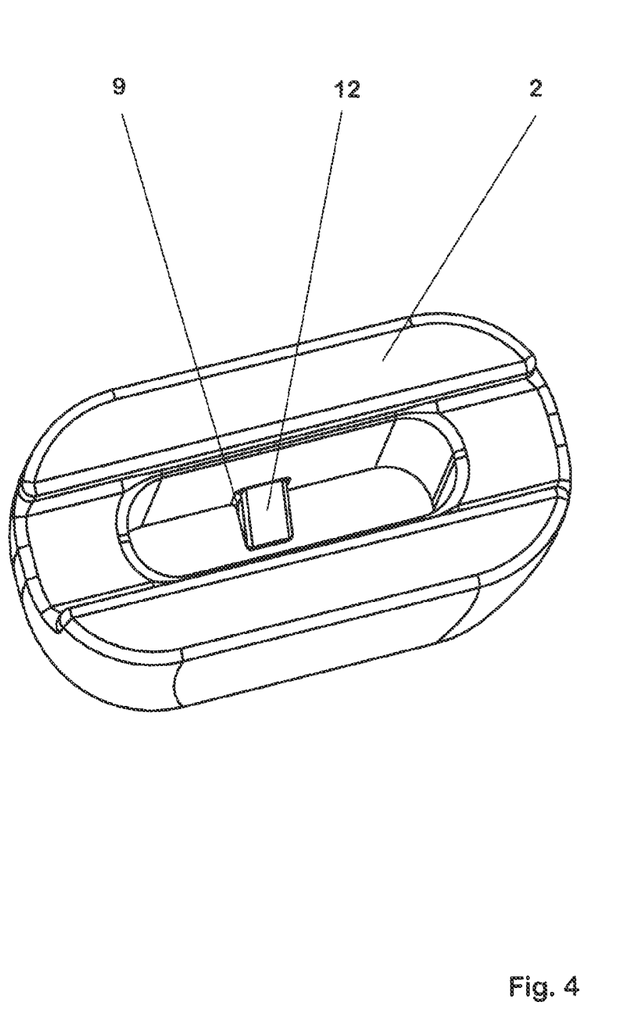
FIG. 4 is a detailed illustration of the slide.
Figure 5:
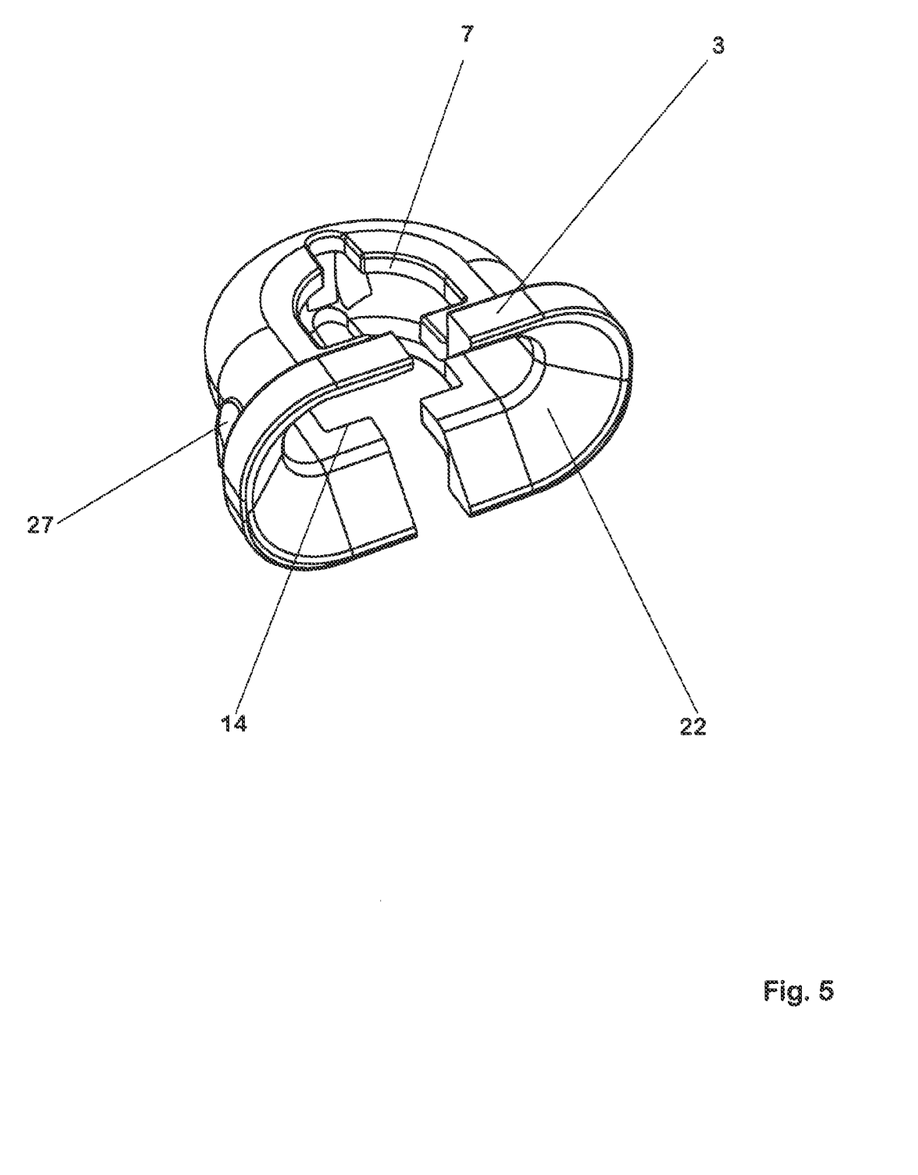
FIG. 5 is a detailed illustration of the receiving pocket.

As illustrated in FIGS. 1 to 5, the clip 1 has as the spring element at least one resilient snap-type hook 5. The locking element (the hook) 6, serves for locking in an opening 7 of the receiving pocket 3, FIG. 2. The snap-type hook 5 is enclosed by a circumferential web 8. The web 8 at the clip 1 serves for guiding and centering in the slide 2 and in the receiving pocket 3. For this purpose, the web 8 has dimensions which essentially correspond to the opening in the slide 2, which serves for receiving the snap-type hook. The snap-type hook itself is constructed thinner than the web 8, and is connected to the clip only in the area of the base of the clip 1 near the strap receiving means 4. By selecting the material, preferably synthetic material, this makes available resilient properties of the snap-type hook 5. The clip 1 has a receiving means 4, through which a strap 29, usually a textile strap, can be guided. The strap can also be fixedly connected to the clip and/or may consist, for example, of synthetic material.

The slide 2 is pushed over the clip 1 and serves as the actuating element for releasing the snap-type connection.

The slide 2 has, for this purpose on its inside, a projection 9 which engages in the opening 10 in the snap-type hook 5. The opening 10 in the snap-type hook 1 has at one side an inclined surface 11. The projection 9 in the slide 2 is also provided with an inclined surface 12. These inclined surfaces 11, 12 serve as inclined planes for coupling and uncoupling the snap-type connection when the slide 2 is pulled/pushed in the direction of the strap eyelet 4. During these movements, the slides 11, 12 slide on top of each other and thereby exert a force on the snap-type hook 5, which is deflected out of its position of rest. However, the same result can also be achieved if projection 9 and opening 10 are exchanged. In the slide 2 is a projection 9 and in the snap-type hook 5 is an opening 10.

Locking of the clip 1 in the pocket 3 takes place by simple insertion. For the insertion, the user can use the slide 2 or the clip 1 as a gripping surface. This does not essentially lead to a relative movement between clip 1 and slide 2 because the movement of the slide 2 on the clip in the direction of the receiving pocket 3 is limited by the projection 9, which engages in the opening 10.

When the clip 1 is inserted into the pocket 3, the locking element 6, constructed as hook 6, slides with its inclined insertion surface downwardly along a corresponding inclined surface at the opening of the pocket 3. Consequently, the snap-type hook 5 is briefly deflected by a wedge and lever action, and facilitates the complete insertion until the hook 6 engages in the area of the opening 7 in an undercut.

When the clip 1 is locked in the receiving pocket 3, this connection cannot be released by pulling forces acting on the clip 4, but rather provides a secure holding of the connection.

For releasing the connection, the slide 2 must be pushed/pulled in the direction of the strap receiving means 4. By displacing the slide 2 relative to the clip 1, the snap-type hook 5 is deflected, so that the connection between hook 6 and the undercut of the opening 7 is released. The deflection is caused by a lever or wedge action exerted by the inclined surfaces 11, 12 on the snap-type hook. The snap-type hook 5 is indirectly actuated. Lateral recesses 30 of the slide 2 formed, together with the strap receiving means 4, an end stop for the movement of the slide so that the slide cannot be pushed past the strap receiving means 4.

The actuating direction of the slide 2 corresponds essentially to the direction in which the clip is pushed into the pocket. The pulling direction of the straps may deviate from this direction. In order to facilitate an optimum adaptation of the mask, the receiving pocket 3 may be mounted moveably at the mask body 26 or the forehead rest 26'. For this purpose, the mask body 26 includes a receiving means 28 for the pocket 3. The pocket is locked at this location with its locking elements 27. Because of the construction of the pocket 3 in a U-shape and because of the flexible material, the pocket can be deformed by a slight pressure in the area of the locking elements 27 and can thereby be easily inserted into the recess 28 in the mask body 26.

The slide 2 may have gripping troughs or gripping surfaces 13 in order to ensure that the user has a sure grip when actuating the slide 2.

The clip 1 can be pushed with two different orientations into the pocket 3 because the pocket 3 is constructed symmetrically and can receive the snap-type hook 5 of the hook 1 in both directions. It must merely be observed that the strap which is threaded into the strap receiving means 4 of the clip 1 is not twisted, since otherwise pressure marks could be formed on the face of the patient.

A rip line can optionally be fastened to one of the slides 2. This rip line serves for a quick separation of the connection, for example, in panic situations. Since the right and left clips 1 are exchangeable, there is the possibility of allowing the quick release system to be used by right-handed or left-handed persons with only one rip line.

When in use, the slide 2 is slid over the guide web 8 of the clip 1 and engages thereover the projection 9 in slide 2, which engages in the opening 10 in the snap-type hook 5. The connection can be disassembled for cleaning the individual parts. It is sufficient for this purpose to apply a slight pressure on the snap-type hook 5, and the locking action of the projection 9 of the slide 2 in the opening 10 of the snap-type hook 5 is released. For the assembly, the slide is once again pushed over the clip 1.

Figure 6:
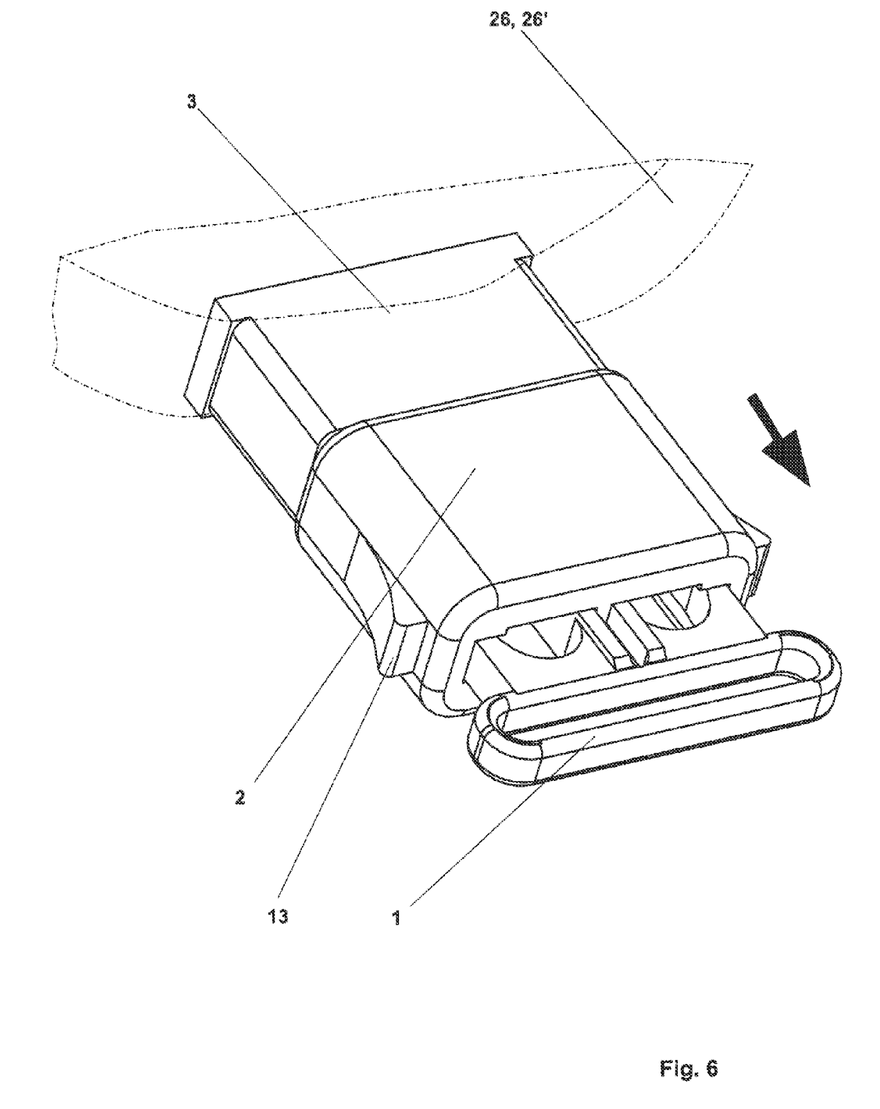
FIG. 6 shows the configuration of a second embodiment of a fastening device.
Figure 7:
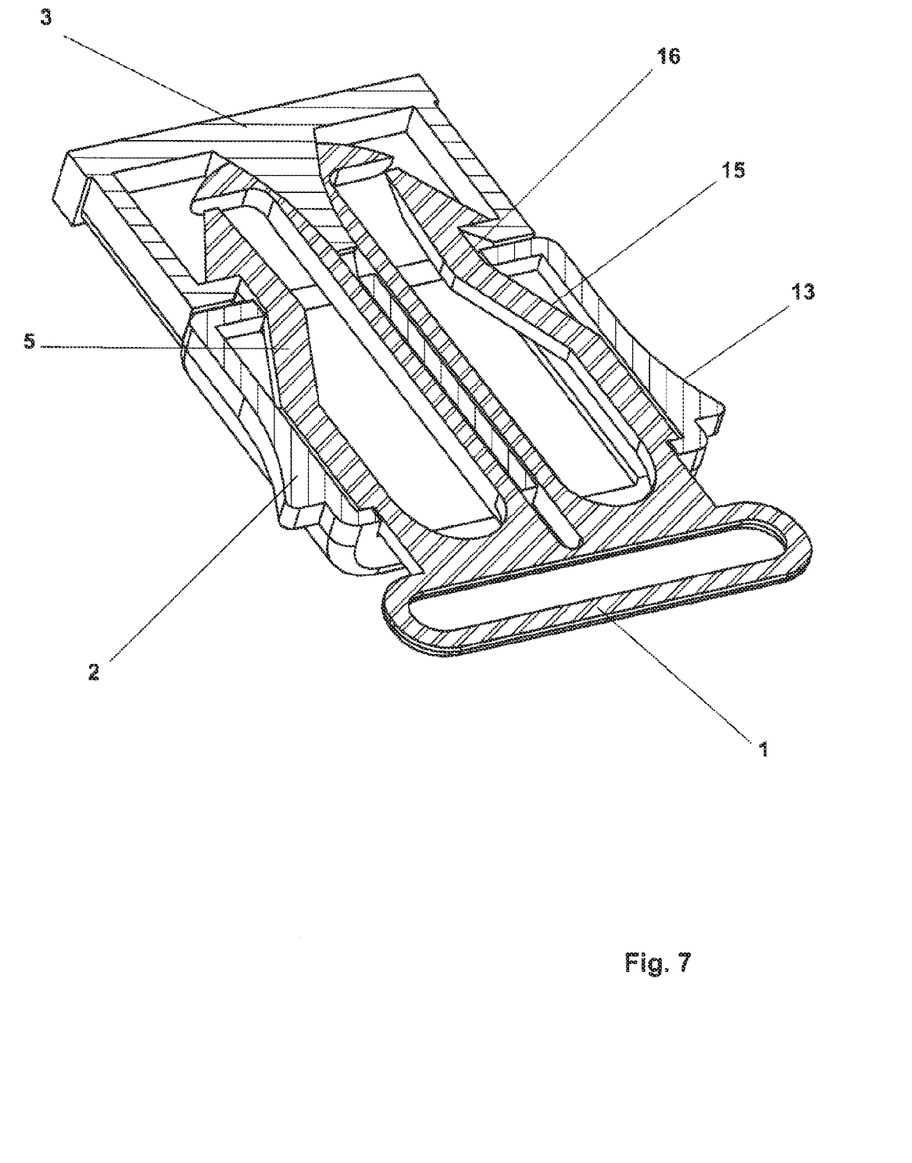
FIG. 7 is a sectional view of the fastening device.
Figure 8:
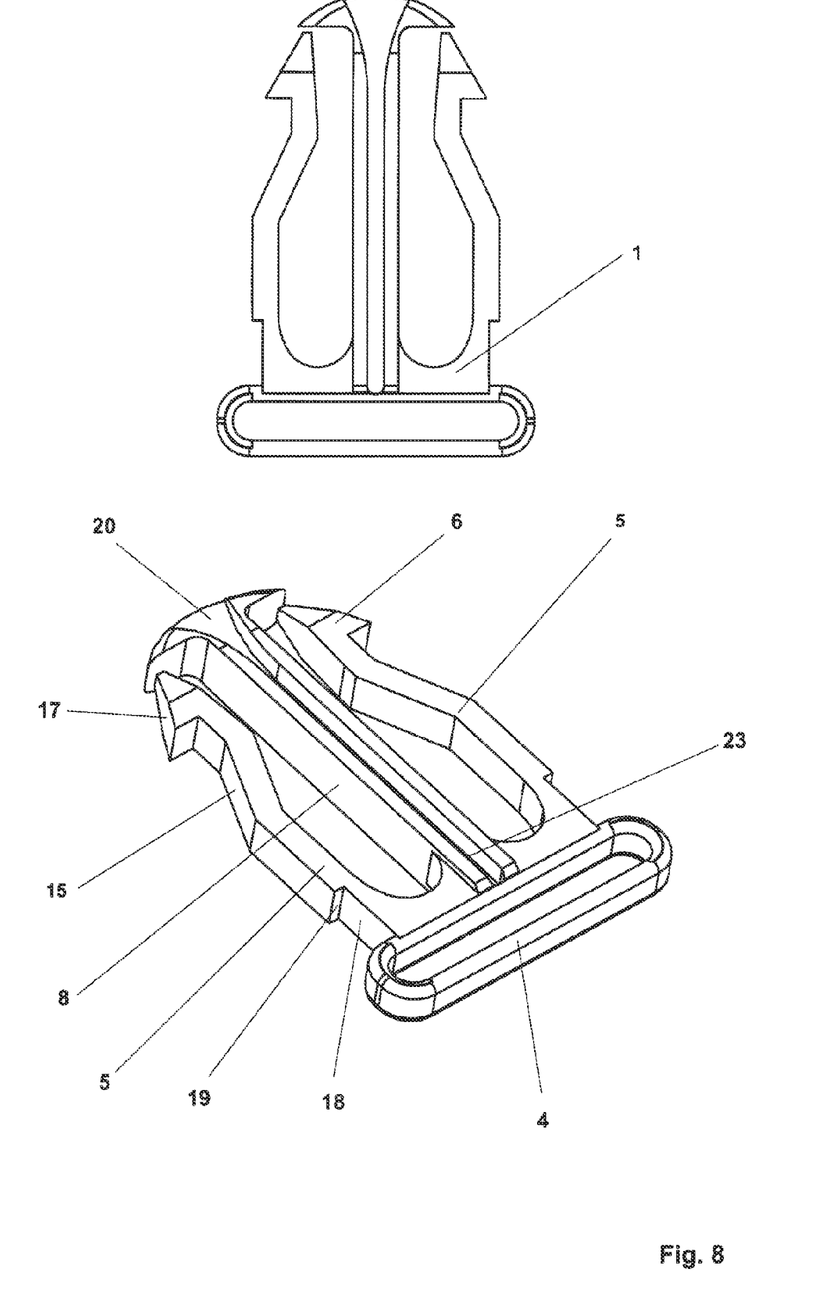
FIG. 8 is a detailed illustration of the clip.
Figure 9:
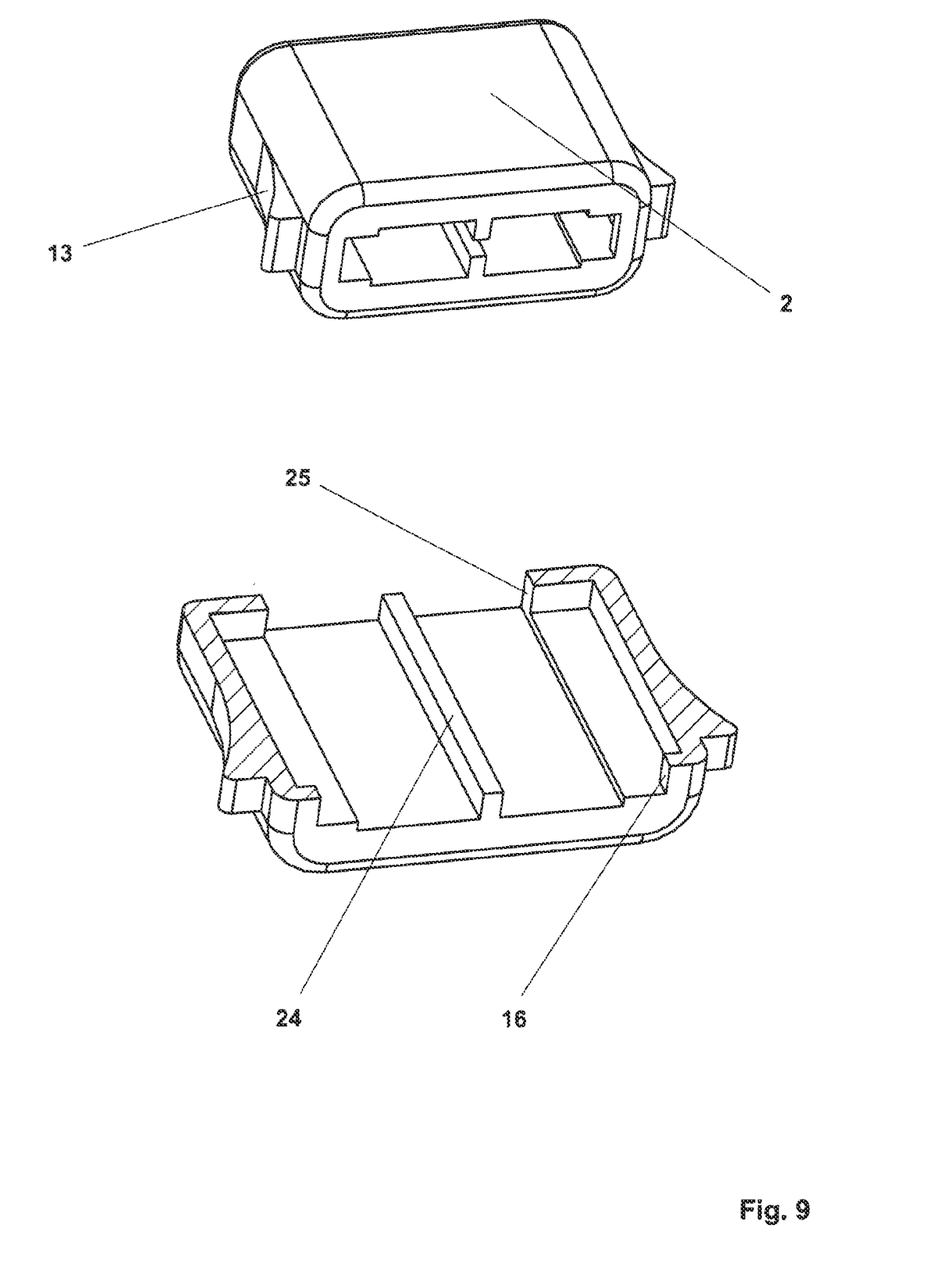
FIG. 9 is a detailed illustration of the slide.
Figure 10:
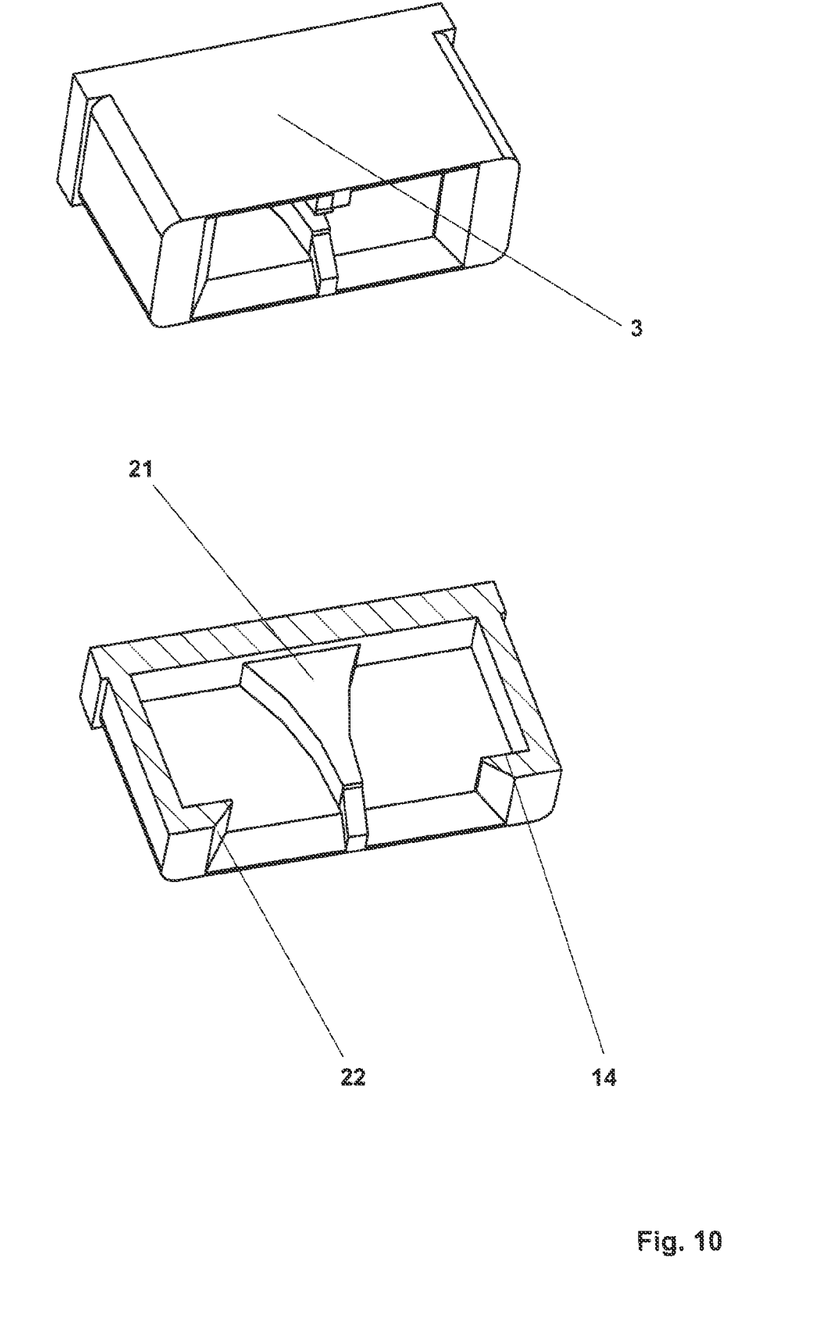
FIG. 10 is a detailed illustration of the receiving pocket.

In FIG. 6 to FIG. 10, the clip 1 has two resilient snap-type hooks 5. These two snap-type hooks 5 rest laterally against the outside of the clip 1. A web 8 serving for guiding and centering is provided in the middle of the clip 1, which is constructed with a greater thickness than the snap-type hooks.

The resilient snap-type hooks 5 have at their ends, locking elements 6, which during the assembly, engage behind an undercut 14 arranged on both sides in the receiving pocket 3, and hold the connection in this manner. These snap-type hooks 5 additionally each have an inclined surface 15. The projection 9, 25 of the slide 2 acts on these inclined surfaces when the slide is pulled/pushed in the direction of the strap eyelet 4, and thereby releases the connection of the hooks 6 of the snap-type hook 5 at the undercut 14 of the pocket 3.

For assembling the slide 2, the slide 2 is pushed over the clip 1. As this happens, the slide 2 is guided over the inclined surfaces 17 at the hook 6 of the snap-type hooks 5, and thereby the slide 2 presses the snap-type hooks 5 slightly together. In this position, the snap eyelet 4, on the one hand, and lateral reduced thickness areas 18 at the snap-type hooks 5, on the other hand, form a stop 19 for the slide 2, so that the slide 2 cannot slip from the clip 1.

The guide web 8 in the middle of the clip 1 has, at an end thereof, an opening 20 into which engages a counter piece 21 of the receiving pocket 3 for guiding and centering. Grooves 23, provided on the upper side and on the lower side in the guide web 8, serve for guiding the slide 2 which has webs 24 which are guided in the grooves 23. The slide 2 has, on the outside, gripping troughs 13 for a simple and secure actuation of the slide 2. For actuating the slide 2 for releasing the connection in the receiving pocket 3, the slide presses with the projection 9, 25 against the lateral inclined surface 15 at the snap-type hooks 5 and thereby deflects the snap-type hooks 5—by a wedge and lever action—and releases the connection. Subsequently, the slide 2 is moved back into its initial position—by the forces from the elastic deformation of the snap-type hooks—and is held there.

Serving as insertion aids for mounting the clip 1 in the receiving pocket 3, are lateral inclined insertion surfaces 22 in the receiving pocket 3.

The clip 1 and the slide 2 are constructed symmetrically so that the connection can be carried out with two different orientations in the receiving pocket 3, which is also symmetrical. Also in this case, a rip line may optionally be mounted for releasing the connection by right-handed and left-handed persons.

Both embodiments described above, operate in accordance with the same principal and offer to the user an easy and secure use when opening and closing the strap at the mask body and/or the forehead rest, and a secure hold of the mask on the head of the user.

Any widely used hard synthetic material, such as, for example, POM, PC or PA, preferably POM, can be used as the material of the clip 1, the slide 2 and the receiving pocket 3. The slide 3 may additionally contain a soft component as a coating or haptic element as a soft component which completely or partially surrounds the outer surface of the slide 3. This, soft component may be connected to the slide by the 2K-method, or may be glued on. This type of fastening device can, of course, also be used in other fields, for example, in the field of medical technology or the consumer sector. For example, buckles or locks for closing medical cases, backpacks, and also for all other types of bags, cases, or backpacks 26" can operate according to the same principle.

REFERENCE NUMERALS

1 Clip
2 Slide
3 Receiving means
4 Strap receiving means
5 Snap-type hook, spring element
6 Hook, locking element
7 Opening in the receiving pocket 3
8 Guide web
9 Surface for deflecting the snap-type hooks, projection
10 Opening in snap-type hook, spring element 5
11 Inclined surface in opening 10
12 Inclined surface at projection 9
13 Gripping trough or gripping surface at slide 2
14 Undercut in receiving pocket 3
15 Inclined surfaces at snap-type hook 5
16 Locking point for stop 19
17 Inclined surface at the hooks 6
18 Reduced thickness portion at snap-type hook
19 Stop for slide 2
20 Opening in guide web 8
21 Guide in the receiving pocket 3
22 Inclined insertion guide surfaces in the receiving pocket 3
23 Grooves in guide web 8
24 Guide webs in slide 2
25 Surface for deflecting the snap-type hook, projection 26, 26', 26" Mask body, forehead rest, backpack, case
27 Locking element at receiving pocket 3
28 Receiving means of receiving pocket 3 in mask body, forehead rest, backpack, case, bag
29 Strap
30 End stop

The invention claimed is:

1. A fastening device for a strap, wherein the fastening device comprises a receiving element; a clip with at least one spring element configured for locking engagement in the receiving element; and a slide that has an opening for receiving the clip, wherein the slide is configured to be directly coupled only to the clip and is moveable relative to the clip, and wherein a movement of the slide moves the at least one spring element out of a position of rest for releasing the locking engagement.

2. The fastening device of claim 1, wherein the at least one spring element comprises at least one projection with an inclined surface that causes the at least one spring element to be deflected out of the position of rest when the slide is moved relative to the clip.

3. The fastening device of claim 1, wherein the slide comprises at least one projection with an inclined surface that deflects the at least one spring element out of the position of rest when the slide is moved relative to the clip.

4. The fastening device of claim 1, wherein the clip comprises at least one guide element along which relative movement of the slide takes place at least partially.

5. The fastening device of claim 1, wherein the at least one spring element comprises at least one locking element that is located at an undercut in an area of the receiving element when the clip and the receiving element are in the locking engagement.

6. The fastening device of claim 1, wherein the at least one spring element of the clip comprises a locking element that engages behind an undercut in the receiving element and thereby forms the locking engagement.

7. The fastening device of claim 1, wherein the receiving element comprises an inclined insertion surface configured so that when the at least one spring element is inserted in the receiving element, the at least one spring element slides along the inclined insertion surface of the receiving element to facilitate complete insertion.

8. The fastening device of claim 1, wherein the receiving element is constructed symmetrically and the at least one spring element of the clip can be pushed into the receiving element in at least two different orientations.

9. The fastening device of claim 1, wherein the clip comprises an end with an eyelet for receiving the strap and, at an opposite end, at least one locking element.

10. The fastening device of claim 9, wherein the locking element is a hook and the receiving element is a pocket having lateral inclined insertion surfaces that act on inclined surfaces of the at least one spring element until the hook engages behind surfaces of the receiving element during insertion of the clip.

11. The fastening device of claim 1, wherein the slide, after deflecting the at least one spring element out of the position of rest, is movable back into an initial position by forces produced by elastic deformation of the at least one spring element.

12. The fastening device of claim 1, wherein the at least one spring element consists of one spring element.

13. The fastening device of claim 1, wherein the at least one spring element is a snap hook.

14. A fastening device for a strap, wherein the fastening device comprises a receiving element; a clip with a spring element that is configured for locking engagement in the receiving element and is partially surrounded by a circumferential web; and a slide that has an opening for receiving the clip and is moveable relative to the clip, and wherein a movement of the slide moves the spring element out of a position of rest for releasing the locking engagement.

15. The fastening device of claim 14, wherein the spring element is a snap hook.

16. The fastening device of claim 15, wherein the snap hook is constructed thinner than the circumferential web and is connected to the clip only in an area of a base of the clip.

17. The fastening device of claim 14, wherein the spring element comprises at least one projection with an inclined surface that causes the spring element to be deflected out of the position of rest when the slide is moved relative to the clip.

18. The fastening device of claim 14, wherein the spring element comprises at least one locking element that is located at an undercut in an area of the receiving element when the clip and the receiving element are in the locking engagement.

19. The fastening device of claim 14, wherein the slide, after deflecting the spring element out of the position of rest, is movable back into an initial position by forces produced by elastic deformation of the spring element.

20. The fastening device of claim 14, wherein the receiving element comprises an inclined insertion surface configured so that when the spring element is inserted in the receiving element, the spring element slides along the inclined insertion surface of the receiving element to facilitate complete insertion.

* * * * *